(12) United States Patent
Mantri et al.

(10) Patent No.: US 10,669,172 B2
(45) Date of Patent: Jun. 2, 2020

(54) ELEMENTAL SULFUR DISPERSANT TO CONTROL FOULING IN WATER SYSTEMS

(71) Applicant: ECOLAB USA, Inc., St. Paul, MN (US)

(72) Inventors: Dinesh Mantri, Pune (IN); David Rodman, Townsville (AU); Jasbir S. Gill, Naperville, IL (US)

(73) Assignee: ECOLAB USA INC., St. Paul, MN (US)

( * ) Notice: Subject to any disclaimer, the term of this patent is extended or adjusted under 35 U.S.C. 154(b) by 102 days.

(21) Appl. No.: 16/106,746

(22) Filed: Aug. 21, 2018

(65) Prior Publication Data

US 2019/0062184 A1 Feb. 28, 2019

Related U.S. Application Data

(60) Provisional application No. 62/549,186, filed on Aug. 23, 2017.

(51) Int. Cl.
*C01B 17/10* (2006.01)
*C02F 1/68* (2006.01)
(Continued)

(52) U.S. Cl.
CPC ............... *C02F 1/68* (2013.01); *C01B 17/10* (2013.01); *C02F 5/12* (2013.01); *C07H 15/04* (2013.01);
(Continued)

(58) Field of Classification Search
CPC ... C01B 17/10; C02F 1/68; C02F 5/12; C07H 15/04; C08L 83/04; C09K 8/532; F24T 50/00
See application file for complete search history.

(56) References Cited

U.S. PATENT DOCUMENTS 4,123,107 A 10/1978 Bryant, Jr. et al.
4,976,937 A 12/1990 Lee et al.
(Continued)

FOREIGN PATENT DOCUMENTS

CN 101301563 11/2008
CN 202052351 U 11/2011
(Continued)

OTHER PUBLICATIONS

Bohon et al., "Novel chemical dispersant for removal of organic/inorganic "Schmoo" scale in produced water injection systems," NACE International: Corrosion 98 Conference Paper No. 73, pp. 1-18 (Year: 1998).*

(Continued)

*Primary Examiner* — Lucas A Stelling
(74) *Attorney, Agent, or Firm* — Eric D. Babych; Barnes & Thornburg LLP

(57) ABSTRACT

A composition and method for dispersing sulfur, cleaning sulfur deposits, and minimizing foaming in an aqueous system is disclosed. The method may include adding a first sulfur dispersant to process water containing sulfur and dispersing the sulfur. The first sulfur dispersant may include a $C_5$-$C_{25}$ alkyl polyglycoside. A second sulfur dispersant may also be added to the process water. The second sulfur dispersant may include a polymer of acrylic acid and 2-acrylamido-2-methylpropane sulfonic acid.

18 Claims, 2 Drawing Sheets

(51) Int. Cl.
*C02F 5/12* (2006.01)
*C07H 15/04* (2006.01)
*C08L 83/04* (2006.01)
*C09K 8/532* (2006.01)
*F24T 50/00* (2018.01)
*C08F 220/06* (2006.01)
*C08F 220/58* (2006.01)
*C02F 103/10* (2006.01)

(52) U.S. Cl.
CPC .......... *C08F 220/06* (2013.01); *C08F 220/58* (2013.01); *C08L 83/04* (2013.01); *C09K 8/532* (2013.01); *C02F 2101/40* (2013.01); *C02F 2103/10* (2013.01); *C02F 2303/12* (2013.01); *C02F 2303/22* (2013.01); *C02F 2305/04* (2013.01); *F24T 50/00* (2018.05)

(56) References Cited

U.S. PATENT DOCUMENTS

| | | | |
|---|---|---|---|
| 5,223,160 | A | 6/1993 | Emmons |
| 5,391,781 | A | 2/1995 | Sintim et al. |
| 5,567,212 | A | 10/1996 | Gentry et al. |
| 5,618,408 | A | 4/1997 | Poirier et al. |
| 5,866,749 | A | 2/1999 | Ou |
| 6,066,304 | A | 5/2000 | Freetly et al. |
| 6,887,445 | B2 | 5/2005 | Braga et al. |
| 6,942,037 | B1 | 9/2005 | Arnold et al. |
| 2004/0259982 | A1 | 12/2004 | Bair et al. |
| 2006/0100127 | A1 | 5/2006 | Meier et al. |
| 2006/0194700 | A1 | 8/2006 | Gatlin et al. |
| 2007/0260041 | A1 | 11/2007 | Crich et al. |
| 2008/0260864 | A1 | 10/2008 | Dascalu |
| 2009/0288822 | A1 | 11/2009 | Eddy et al. |
| 2011/0236450 | A1 | 9/2011 | Scheuing et al. |
| 2012/0080641 | A1 | 4/2012 | Relenyi |
| 2012/0285893 | A1* | 11/2012 | Moore ............ C02F 1/52 210/723 |
| 2014/0374104 | A1 | 12/2014 | Seth |
| 2015/0011453 | A1 | 1/2015 | Bennett et al. |
| 2015/0013987 | A1 | 1/2015 | Underwood et al. |
| 2015/0037202 | A1 | 2/2015 | Harrington et al. |
| 2015/0119300 | A1 | 4/2015 | Andrecola |
| 2015/0275627 | A1 | 10/2015 | Xu et al. |
| 2016/0002522 | A1 | 1/2016 | Gaertner et al. |
| 2016/0208074 | A1 | 7/2016 | Ogi et al. |
| 2016/0312141 | A1 | 10/2016 | Rana et al. |
| 2017/0066977 | A1 | 3/2017 | Rana et al. |
| 2017/0088505 | A1 | 3/2017 | Harrington et al. |

FOREIGN PATENT DOCUMENTS

| | | |
|---|---|---|
| CN | 102304783 | 1/2012 |
| CN | 102382700 | 3/2012 |
| CN | 102397744 A | 4/2012 |
| CN | 102653706 | 9/2012 |
| CN | 102921282 | 2/2013 |
| CN | 103865505 A | 6/2014 |
| CN | 104877656 A | 9/2015 |
| CN | 104910886 | 9/2015 |
| CN | 104923001 A | 9/2015 |
| CN | 105084319 | 11/2015 |
| CN | 105498494 | 4/2016 |
| CN | 105937387 | 9/2016 |
| DE | 3340962 | 6/1984 |
| DE | 19904014 | 8/2000 |
| DE | 19934167 A1 | 1/2001 |
| EP | 1361480 | 11/2003 |
| FR | 2953713 | 6/2011 |
| FR | 3004643 | 10/2014 |
| FR | 3015242 | 6/2015 |
| JP | H05230090 A | 9/1993 |
| JP | H11279192 A | 10/1999 |
| JP | 2000128895 | 5/2000 |
| JP | 2011207988 | 10/2011 |
| WO | WO 0101949 | 1/2001 |
| WO | WO 02102931 A2 | 12/2002 |
| WO | WO 03055578 | 7/2003 |
| WO | WO 2011069949 | 6/2011 |
| WO | WO 2013176803 A1 | 11/2013 |
| WO | WO 2014186174 | 11/2014 |
| WO | WO 2015091743 | 6/2015 |
| WO | WO 2015150971 A1 | 10/2015 |
| WO | WO 2016092541 A1 | 6/2016 |

OTHER PUBLICATIONS

Drzymala, Jan et al., "Effect of the molecular weight of polysaccharides containing D-glucose repeating units with α-glycoside bonds on the selectivity of lead removal from a copper-ore concentrate" Prace Naukowe Instytutu Gornictwa Politechniki Wroclawskiej (2004) 106: 31-43 (English Abstract).

Fisher, Kevin S. et al., "GRI Sulfur Scavenging Technology Research" The Sixth Gas Research Institute Sulfur Recovery Conference (Austin, May 15-17, 1994) 229-256.

Liu, Yue-Long et al., "The Dispersion Stability of Polyacrylic Copolymers with Three Anionic Sulfonic Groups on Nano Zinc Oxide" Applied Mechanics and Materials (2014) 692: 292-295.

Dalrymple, Dennis "Hybrid Sulfur Recovery Process for Natural Gas Upgrading Quarterly Technical Report" CrystalTech, Inc. (2003) 9 pages.

Han, Zhiguo et al., "Micellar and Interfacial Behavior of Mixed Systems Containing Glycoside-Based Surfactant and Cationic Didecyldimethylammonium Chloride" J Surfact Deterg (2015) 18:873-880.

Hidayat, Ismail et al., "Increased Generation Performances by Using Sulfur Dispersant in the Cooling Tower at the Wayang Windu Geothermal Power Plant (A Lesson Learned from Wayang Windu Geothermal Power Plant Operation)" GRC Transactions, (2016) 40: 829-837.

Liu, Y.M. et al., "A non-phosphorus water treatment agent in water injection system: Inhibiting strontium sulfate and dispersing ferric oxide" Water Science and Technology: Water Supply (2017) 17(2): 352-361.

Miller, D., "Removal of Sulfur Compounds From Natural Gas and Liquid Streams by Use of Scavengers" GPA Panhandle Plains Reg. Mtg. (Amarillo, Texas, Sep. 27, 1990) PAP 1990 (10 pp).

Tietze, Lutz F. et al., "Liquid-Crystalline D-Glucose Dialkyl Acetals and Dodecyl D-Glucofuranosides" Chemische Berichte (1994), 127(6): 1065-1068.

International Search Report and Written Opinion for PCT/US2018/047205, dated Oct. 10, 2018, 14 pages.

\* cited by examiner

ELEMENTAL SULFUR DISPERSANT TO CONTROL FOULING IN WATER SYSTEMS

BACKGROUND

1. Field of the Invention

The present invention generally relates to dispersing sulfur. More particularly, the present disclosure relates to a composition and methods for dispersing sulfur and minimizing foaming in an aqueous system.

2. Description of the Related Art

Geothermal energy is energy in the form of heat within the earth's interior, which can be tapped using geothermal wells. The earth's interior contains an enormous supply of heat, but challenges remain in extracting the heat for generating energy. Geothermal energy moves towards the earth's surface by thermal conduction through solid rock. Thermal energy can also be transmitted towards the earth's surface by movement of molten rock or by circulation of fluid ($H_2O$ as steam or water) through interconnected fractures and pores. Geothermal wells are in any instance relatively deep wells.

Geothermal brines and steam are generally used as the energy source. Geothermal brine is used in power generation, heating and electrical processes. Geothermal steam temperatures range from about 185° C. to about 370° C. (about 365° F. to about 700° F.). Steam is separated from the brine using flashing units. Low temperature brines can also be used to produce electricity binary units (secondary fluid units). The geothermal brines can have a salinity from less than about 1000 ppm to several hundred thousand ppm, and a content of non-condensable gases up to about 6 percent. Depending upon the salt content and application, geothermal fluids may be used directly or through a secondary fluid cycle. The use of geothermal energy as an energy source has risen in importance as other energy sources become less abundant and more expensive. This is a sustainable renewable source of energy, and unlike other renewable sources, geothermal energy is constantly available.

Mineral deposition is a major problem under the severe conditions encountered in the production of geothermal energy and can be a factor limiting the development of geothermal fields. Mineral deposition from the boiling geothermal fluid of a water-dominated reservoir is particularly a problem.

Hydrogen sulfide ($H_2S$) is a naturally occurring contaminant of fluids or produced by sulfur reducing bacteria. The corrosive nature of $H_2S$ causes the accumulation of particulate iron sulfide. Iron compounds, including iron sulfide, can form within pipeline networks that transport gas, oil, water and mixtures of gas, oil and water. The iron sulfide compounds are physically characterized as appearing to be amorphous solid particles capable of absorbing water.

Hydrogen sulfide can be oxidized to produce elemental sulfur that can cause fouling. The oxidized $H_2S$ forms precipitate or scale that deposits on the surfaces of process equipment that contacts the process water containing the sulfide or sulfur compounds. Elemental sulfur originates from oxidation of $H_2S$ and from the presence of microbes in the water. Elemental sulfur can form deposits and cause fouling of process equipment that handles geothermal cooling water.

In the geothermal industry, the condensed steam is generally used as make-up water to the cooling system. The condensed steam contains impurities such as $H_2S$, ammonia, and carbon dioxide. Direct contact condensing systems are generally used in geothermal plants. In direct contact condensing systems, the coolant may be brought into direct contact with the vapor, this kind of cooling system may be suitable for applications where the vapor and the coolant can be mixed together. Examples of direct contact condensing systems include, but are not limited to, spray condenser, baffled column, packed column, jet condenser, and sparge pipe. Since the steam and cooling water mix are in direct contact in condensing systems, the cooling water becomes contaminated with $H_2S$. This sulfide contamination results in sulfur deposition through bio-oxidation and bio-fouling in geothermal cooling water.

Elemental sulfur forms in geothermal cooling water through both chemical and biochemical means. The chemical formation of sulfur from $H_2S$ occurs through direct oxidation by either oxygen in the water or from added oxidants, and the oxidation reaction is temperature and pH dependent. The formation of $S^o$ through biochemical means is much more complicated and can proceed via numerous reaction pathways depending on the bacterial species involved. Controlling the formation of elemental sulfur from $H_2S$ can be more difficult in the case of chemical conversion compared to microbial conversion. Microbial conversion can be controlled to some extent via use of effective biocides.

Microbiological sulfur oxidation results in the formation of elemental sulfur that is either deposited internally within bacterial cells or externally as a crystal. When deposited externally, the sulfur crystals are then colonized by other bacteria that further oxidize the sulfur to sulfate and ultimately form sulfuric acid. The formation of sulfuric acid results in pH reduction in the cooling water to levels that are damaging to the cooling system materials of construction.

Elemental sulfur is also highly hydrophobic causing elemental sulfur particles to aggregate rapidly and form tenacious deposits. Typical deposition spots include cooling tower nozzles, cooling tower fill, spray nozzles in the direct condensers and auxiliary heat exchangers. These deposits can lead to cooling tower fill collapse, blockages in cooling water distribution pipework resulting in loss of cooling efficiency, blockages of nozzles within the condenser that can affect condensation performance (power production), increase in condenser back pressure, and increase steam consumption and total operating cost (steam cost & maintenance cost).

BRIEF SUMMARY

In some embodiments, a method of dispersing sulfur is disclosed. The method may include adding a first sulfur dispersant to process water containing sulfur and dispersing the sulfur. The first sulfur dispersant may include a $C_5$-$C_{25}$ alkyl polyglycoside.

In some embodiments, the method may include adding a second sulfur dispersant to the process water.

In some embodiments, the method may include blending the first sulfur dispersant and the second sulfur dispersant to form a dispersant mixture before addition to the process water.

In some embodiments, the method may include adding an anti-foaming agent to the process water.

In some embodiments, the first sulfur dispersant may include a $C_{10\text{-}16}$ alkyl polyglycoside.

In some embodiments, the first sulfur dispersant may include a $C_{10-16}$ alkyl polyglycoside and a $C_{8-10}$ alkyl polyglycoside.

In some embodiments, the first sulfur dispersant may be added to the process water in an amount of about 1 ppm to about 1000 ppm.

In some embodiments, the first sulfur dispersant may be added to the process water in an amount of about 1 ppm to about 10 ppm.

In some embodiments, the second sulfur dispersant may include a polymer that may include acrylic acid and 2-acrylamido-2-methylpropane sulfonic acid.

In some embodiments, the second sulfur dispersant may be added to the process water in an amount of about 2 ppm to about 100 ppm.

In some embodiments, the second sulfur dispersant may be added to the process water in an amount of about 2 ppm to about 15 ppm.

In some embodiments, the polymer may have a weight average molecular weight of about 5,000 Da to about 50,000 Da.

In some embodiments, the polymer that may include about 50-70 wt % acrylic acid and about 30-50 wt % 2-acrylamido-2-methylpropane sulfonic acid.

In some embodiments, the dispersant mixture may include from about 5% to about 95% by weight of the first sulfur dispersant and from about 95% to about 5% by weight of the second sulfur dispersant.

In some embodiments, the anti-foaming agent may be selected from of a $C_5$-$C_{25}$ alkyl alcohol, a $C_5$-$C_{25}$ alkyl alcohol ethoxylate, monobasic aluminum stearate, stearic acid, polydimethylsiloxane, sorbitan monostearate, hydrated silica, ethoxylated sorbitan monostearate, xanthan gum, amorphous silica, and any combination thereof.

In some embodiments, the anti-foaming agent may include polydimethylsiloxane and sorbitan monostearate.

In some embodiments, the process water may be geothermal cooling water or geothermal condensate.

In some embodiments, the sulfur may be elemental sulfur.

In other embodiments, a use of a first dispersant in geothermal cooling water for dispersing sulfur is disclosed. The first dispersant may include a $C_5$-$C_{25}$ alkyl polyglycoside.

In certain embodiments, a method of dispersing sulfur in geothermal cooling water is disclosed. The method may include adding a first sulfur dispersant that may include $C_5$-$C_{25}$ alkyl polyglycoside to the geothermal cooling water containing sulfur; adding a second sulfur dispersant that may include a polymer comprising acrylic acid and 2-acrylamido-2-methylpropane sulfonic acid to the geothermal cooling water; and dispersing the sulfur.

In some embodiments, the first sulfur dispersant is added before the second sulfur dispersant, after the second sulfur dispersant, and/or as a mixture with the second sulfur dispersant.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE DRAWINGS

A detailed description of the invention is hereafter described with specific reference being made to the drawings in which.

DETAILED DESCRIPTION

Figure 1:
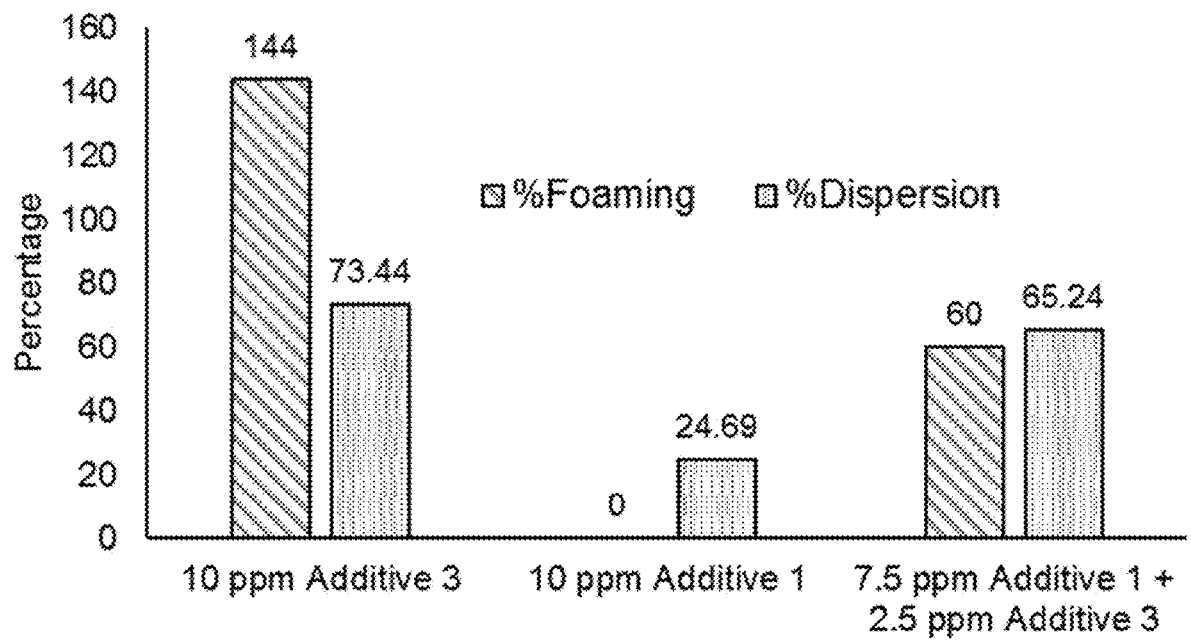
FIG. 1 shows percent dispersion and percent foaming for two different additives alone and in combination.

Various embodiments are described below. The relationship and functioning of the various elements of the embodiments may better be understood by reference to the following detailed description. However, embodiments are not limited to those illustrated below. In certain instances details may have been omitted that are not necessary for an understanding of embodiments disclosed herein.

Dispersants, especially bio-dispersants, have surfactant properties and are foaming in nature. Foaming is not acceptable in direct contact type condensing application because it results in loss of vacuum in the power generation system and result in plant shutdowns.

Elemental sulfur can be dispersed using a sulfur dispersant; however, the dispersant can cause significant foam formation. Foam formation causes significant problems in some industrial processes—especially in geothermal cooling towers. The subject matter of the present disclosure addresses sulfur fouling and dispersant foam generation in aqueous systems. Specifically, the subject matter discloses compositions and methods of dispersing sulfur while minimizing foam generation.

Generally, sulfur deposit fouling may be addressed by cleaning existing deposits or by preventing their formation. The compositions and methods disclosed herein are effective at cleaning existing sulfur deposits and preventing or inhibiting formation of sulfur deposits. In addition to cleaning and preventing sulfur deposits, the compositions and methods disclosed herein are effective in reducing foam formation in the treated process water.

In some embodiments, a method of dispersing sulfur is disclosed. The method may include adding a first sulfur dispersant to process water containing sulfur and dispersing the sulfur. The first sulfur dispersant may include a $C_5$-$C_{25}$ alkyl polyglycoside. Alkyl polyglycosides are non-ionic and may include a hydrophilic sugar and an alkyl group of variable carbon chain length that is hydrophobic. As used herein "disperse" and "dispersing" denote suspending solids in a fluid, removing solids from a surface, or maintaining solids in a fluid suspension.

Unless otherwise indicated, "alkyl" as described herein alone or as part of another group is an optionally substituted linear saturated monovalent hydrocarbon radical or an optionally substituted branched saturated monovalent hydrocarbon radical. Linear or branched alkyl groups may have anywhere from 1 or 3 to 32 carbon atoms. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, i-hexyl, s-hexyl, t-hexyl, and the like.

In some embodiments, the first sulfur dispersant may include a $C_{10-16}$ alkyl polyglycoside. In certain embodiments, the first sulfur dispersant may be $C_{12}$ alkyl polyglycoside, $C_{13}$ alkyl polyglycoside, $C_{14}$ alkyl polyglycoside, $C_{15}$ alkyl polyglycoside, $C_{16}$ alkyl polyglycoside, and any combination thereof.

In some embodiments, the first sulfur dispersant may be a mixture of two alkyl polyglycosides with different alkyl chain lengths such as $C_{10-16}$ alkyl polyglycoside and $C_{8-10}$ alkyl polyglycoside. When the first sulfur dispersant is a mixture of two or more alkyl polyglycosides, then the alkyl polyglycosides may be added separately at the same or different locations or they may be mixed together before addition into the process water. In certain embodiments, the first sulfur dispersant consists of water, $C_{10-16}$ alkyl polyglycoside, and $C_{8-10}$ alkyl polyglycoside.

In some embodiments, the first sulfur dispersant may be added to the process water in an amount of about 0.01 ppm to about 1000 ppm, about 0.01 ppm to about 500 ppm, about 0.01 ppm to about 250 ppm, about 0.01 ppm to about 150 ppm, about 0.01 ppm to about 50 ppm, about 0.01 ppm to about 25 ppm, about 0.01 ppm to about 5 ppm, or about 0.1 ppm to about 2 ppm. In some embodiments, the first sulfur dispersant may be added to the process water in an amount of about 1 ppm to about 10 ppm.

In some embodiments, the method may include adding a second sulfur dispersant to the process water. The second sulfur dispersant may be added simultaneously with the first sulfur dispersant.

In some embodiments, the second sulfur dispersant may be a polymer that may include acrylic acid and 2-acrylamido-2-methylpropane sulfonic acid.

In some embodiments, the second sulfur dispersant may be a polymer comprising about 50-70 wt % acrylic acid and about 30-50 wt % 2-acrylamido-2-methylpropane sulfonic acid.

In some embodiments, the second sulfur dispersant may be added to the process water in an amount of about 2 ppm to about 100 ppm. In some embodiments, the second sulfur dispersant may be added to the process water in an amount of about 0.1 ppm to about 1000 ppm, about 0.1 ppm to about 500 ppm, about 0.1 ppm to about 250 ppm, about 0.1 ppm to about 150 ppm, about 0.1 ppm to about 50 ppm, about 0.1 ppm to about 25 ppm, or about 0.1 ppm to about 5 ppm. In some embodiments, the second sulfur dispersant may be added to the process water in an amount of about 2 ppm to about 15 ppm.

In some embodiments, the polymer may have a weight average molecular weight of about 5,000 Da to about 50,000 Da. In some embodiments, the polymer may have a weight average molecular weight of about 20,000 Da.

In some embodiments, the method may include blending the first sulfur dispersant and the second sulfur dispersant to form a dispersant mixture before addition to the process water. In some embodiments, the dispersant mixture may contain water. The dispersant mixture may contain sodium sulfate and sodium bisulfite. In certain embodiments, the dispersant mixture consists of water, first sulfur dispersant, and second sulfur dispersant.

In some embodiments, the dispersant mixture may include from about 5% to about 95% by weight of the first sulfur dispersant and from about 95% to about 5% by weight of the second sulfur dispersant. In certain embodiments, the relative amount by weight of first sulfur dispersant and second sulfur dispersant added to the process water may range from about 1:10 to about 10:1, about 1:10 to about 1:1, or about 1:5 to about 1:1. In some embodiments, the weight ratio of first sulfur dispersant to second sulfur dispersant added to the process water may be about 1:3.

In some embodiments, the method may include adding an anti-foaming agent to the process water. Examples of anti-foaming agents include, but are not limited, to $C_5$-$C_{25}$ alkyl alcohol, $C_5$-$C_{25}$ alkyl alcohol ethoxylate, monobasic aluminum stearate, stearic acid, polydimethylsiloxane, sorbitan monostearate, hydrated silica, ethoxylated sorbitan monostearate, xanthan gum, and amorphous silica. In some embodiments, the anti-foaming agent may include water, polydimethylsiloxane, and sorbitan monostearate. In other embodiments, the anti-foaming agent may consist of water, polydimethylsiloxane, sorbitan monostearate, hydrated silica, ethoxylated sorbitan monostearate, and xanthan gum.

In some embodiments, the anti-foaming agent may be added to the process water in an amount of about 0.001 ppm to about 100 ppm. In some embodiments, the anti-foaming agent may be added to the process water in an amount of about 0.001 ppm to about 10 ppm, about 0.001 ppm to about 5 ppm, about 0.01 ppm to about 10 ppm, about 0.05 ppm to about 5 ppm, about 0.05 ppm to about 2 ppm, about 0.05 ppm to about 10 ppm, or about 0.1 ppm to about 1 ppm.

In some embodiments, the process water may be geothermal cooling water or geothermal condensate.

In some embodiments, the sulfur may be elemental sulfur.

In other embodiments, a use of a first dispersant in geothermal cooling water for dispersing sulfur is disclosed. The first dispersant may include a $C_5$-$C_{25}$ alkyl polyglycoside. The use may also include using a second sulfur dispersant to disperse sulfur and reduce foaming.

In certain embodiments, a method of dispersing sulfur in geothermal cooling water is disclosed. The method may include adding a first sulfur dispersant to the geothermal cooling water containing sulfur; adding a second sulfur dispersant to the geothermal cooling water; and dispersing the sulfur.

In some embodiments, the dispersant mixture, first dispersant, or second dispersant may include additional additives, such as a hydrogen sulfide scavenger, a corrosion inhibitor, a gas hydrate inhibitor, a biocide, a surfactant, a solvent, an inert tracer, or any combination thereof.

In other embodiments, the dispersants disclosed herein may include one or more corrosion inhibitors, one or more other scale inhibitors, one or more fluorescent tracers, one or more water treatment polymers, one or more polyalkoxy compounds, or any other suitable additive or additional component. In alternative embodiments, such additives may be added simultaneously or sequentially with the dispersants disclosed herein.

In some embodiments, the composition may include an inert tracer, making it compatible with fluorescent tracing technology such 3D TRASAR® technology (available from Ecolab, Inc.). In other embodiments, an inert fluorescent tracer may be included in the composition to provide a means of determining the dosage level. A known proportion of the fluorescent tracer may be added either simultaneously or sequentially with the dispersants or anti-foaming agents. Effective inert fluorescent tracers may include those substances that are chemically non-reactive with other components in the system and that do not significantly degrade with time.

Representative inert fluorescent tracers include fluorescein or fluorescein derivatives; rhodamine or rhodamine derivatives; naphthalene sulfonic acids (mono-, di-, tri-, etc.); pyrene sulfonic acids (mono-, di-, tri-, tetra-, etc.); stilbene derivatives containing sulfonic acids (including optical brighteners); biphenyl sulfonic acids; phenylalanine; tryptophan; tyrosine; vitamin B2 (riboflavin); vitamin B6 (pyridoxin); vitamin E (a-tocopherols); ethoxyquin; caffeine; vanillin; naphthalene sulfonic acid formaldehyde condensation polymers; phenyl sulfonic acid formaldehyde condensates; lignin sulfonic acids; polycyclic aromatic hydrocarbons; aromatic (poly)cyclic hydrocarbons containing amine, phenol, sulfonic acid, carboxylic acid functionalities in any combination; (poly)heterocyclic aromatic hydrocarbons having N, O, or S; a polymer containing at least one of the following moieties: naphthalene sulfonic acids, pyrene sulfonic acids, biphenyl sulfonic acids, or stilbene sulfonic acids.

In certain embodiments, an iron catalyst may be added to the process water. In other embodiments, an iron catalyst is not added to the process water. Iron catalyst may include iron salt, iron complexes, or combinations thereof. Iron catalysts may be, for example, ferrous sulfate, ferric sulfate, ferric chloride, ferrous gluconate, ferric nitrate, iron (III) hydroxide oxide [FeO(OH)], ferrous chloride, ferrous iodide, iron sulfide, iron 4-cyclohexyl-butyrate, ferric oxide, ferric bromide, ferrous fluoride, iron powder, ferrous acetate, ferrous oxalate, ferric oxalate, and the like.

In certain embodiments, hydrogen peroxide may be added to the process water. In other embodiments, hydrogen peroxide is not added to the process water.

EXAMPLES

Example 1

Elemental sulfur was synthesized in-situ by oxidizing sulfide with sodium hypochlorite (bleach). Dispersion was calculated based on transmittance measurement. Dispersion efficiency was calculated using the following formula: Dispersion Efficiency %=$(T_{blank}-T_{final})/(T_{blank}-T_0)$ where $T_{blank}$ was the final transmittance of blank test, $T_0$ was the lowest transmittance of the blank test, and $T_{final}$ was the final transmittance of the test with dispersant (about 3 day incubation time)

To generate elemental sulfur in situ, about 489 ml of deionized water was added into a bottle, and then the required amount of sulfide solution and bleach solution was added into the above beaker to get about 5 ppm sulfide and about 11 ppm free chlorine solution. The solution was stirred for about 30 seconds.

Then, the required amount of dispersant solution was added to the bottle containing the elemental sulfur, and stirred for about another 30 seconds to mix the solution. Table 1 shows the various dispersant compositions tested. The pH was adjusted to about 6.5, and then stirring was stopped the bottle was maintained at room temperature. A blank test without any dispersant was set up at the same time.

Transmittance was measured for the blank solution after an hour. Typically, the lowest transmittance will appear in an hour while sulfur is precipitating but has not yet settled to the bottom of the bottle. After about 3 days, the transmittance was measured and recorded.

TABLE 1

| Additive Compositions | |
| --- | --- |
| Additive Identification | Additive Components |
| Additive 1 | About 52.18 wt % water; about 47.58 wt % copolymer of acrylic acid and 2-Acrylamido-2-methylpropane sulfonic acid; about 0.23 wt % sodium sulfate; about 0.01 wt % sodium bisulfite; trace amount of pyrenetetrasulfonic acid tetrasodium salt |

TABLE 1-continued

| Additive Compositions | |
| --- | --- |
| Additive Identification | Additive Components |
| Additive 2 | About 56.5 wt % water; about 39.6 wt % sulfomethylated polymer of acrylic acid, sodium acrylate, and acrylamide; about 3 wt % sodium formaldehyde bisulfite; about 0.7 wt % methanol; about 0.2 wt % pyrenetetrasulfonic acid sodium salt |
| Additive 3 | About 50 wt % water; about 16.7 wt % $C_{10-16}$ alkyl polyglycoside; about 33.3 wt % $C_{8-10}$ alkyl polyglycoside |
| Additive 4 | About 80 wt % water; about 20 wt % copolymer of ethylene oxide and propylene oxide |
| Additive 5 | About 45 wt % copolymer of ethylene oxide and propylene oxide; about 45 wt % ethoxylated nonylphenol; about 10 wt % water |
| Additive 6 | About 50 wt % tetradecyl phosphonium chloride; about 50 wt % water |
| Additive 7 | About 87 wt % water; about 9 wt % poly(dimethylsiloxane); about 1.4 wt % sorbitan monostearate; about 1 wt % hydrated silica; about 0.8 wt % ethoxylated sorbitan monostearate; about 0.6 wt % xanthan gum |

Table 2 summarizes the transmittance percentage along with sulfur dispersion efficiency. Excluding blank samples, all other samples contain 10 ppm active product. All the tests were carried out in duplicate to confirm repeatability.

TABLE 2

| Transmittance % and sulfur dispersion efficiency | | | | |
| --- | --- | --- | --- | --- |
| | % Transmittance | | | |
| Sample | I | II | Average | % Dispersion |
| Initial Blank ($T_0$) | 74.80 | 74.00 | 74.40 | — |
| Final Blank ($T_{blank}$) | 96.80 | 98.40 | 98.50 | — |
| Additive 1 | 92.70 | 92.40 | 92.55 | 24.69 |
| Additive 2 | 96.60 | 96.70 | 96.65 | 7.68 |
| Additive 3 | 82.20 | 79.40 | 80.80 | 73.44 |
| Additive 4 | 94.70 | 95.40 | 95.05 | 14.32 |
| Additive 5 | 97.20 | 96.10 | 96.65 | 7.68 |
| Additive 6 | 98.10 | 98.00 | 98.05 | 1.87 |

Another experiment was performed to test the combination of Additive 1 and Additive 3. Table 3 summarizes the transmittance and elemental sulfur dispersion for the combination of Additive 1 and 3 and their individual results.

TABLE 3

| Transmittance % and sulfur dispersion efficiency | | | | |
| --- | --- | --- | --- | --- |
| Sample | % Transmittance | | | % Dispersion |
| Initial Blank ($T_0$) | 73.05 | 72.80 | 72.93 | — |
| Final Blank ($T_{blank}$) | 95.65 | 98.10 | 96.88 | — |
| 7.5 ppm Additive 1 + 2.5 ppm Additive 3 | 81.50 | 81.0 | 81.25 | 65.24 |
| 10 ppm Additive 1 | 92.70 | 92.4 | 92.55 | 24.69 |
| 10 ppm Additive 3 | 82.20 | 79.4 | 80.8 | 73.44 |

Example 2

The amount of foaming generated by each dispersant composition was also tested. About 10 ppm (active) Additive 3 was added to about 500 ml of water in a tall measuring cylinder. Nitrogen gas ($N_2$) was purged into the solution at constant flow rate for about 3 minutes. Due to $N_2$ purging, foam forms and the total volume of sample in cylinder will increase. After about 3 minutes, the height (volume) of sample was measured and a % increase in foaming was calculated. Table 4 shows the initial and final volumes for each test and the percent increase in foaming. FIG. 1 shows how percent dispersion and percent foaming is impacted by the combination of Additive 1 and Additive 3 compared to the Additives alone.

TABLE 4

Foaming percentage for Additive 1 and Additive 3

| Sample | Initial Volume (ml) | Final Volume after 3 minute purge (ml) | Increase in foaming volume (ml) | % Increase in foaming volume |
|---|---|---|---|---|
| 10 ppm Additive 3 | 500 | 1220 | 720 | 144 |
| 10 ppm Additive 1 | 500 | 500 | 0 | 0 |
| 7.5 ppm Additive 1 + 2.5 ppm Additive 3 | 500 | 800 | 300 | 60 |

The blend of about 2.5 ppm active of Additive 3 and about 7.5 ppm active of Additive 1 had significantly less foaming (about 60% less than Additive 3 alone) yet only about 8% reduction in dispersion capability compared to Additive 3.

Example 3

Figure 2:
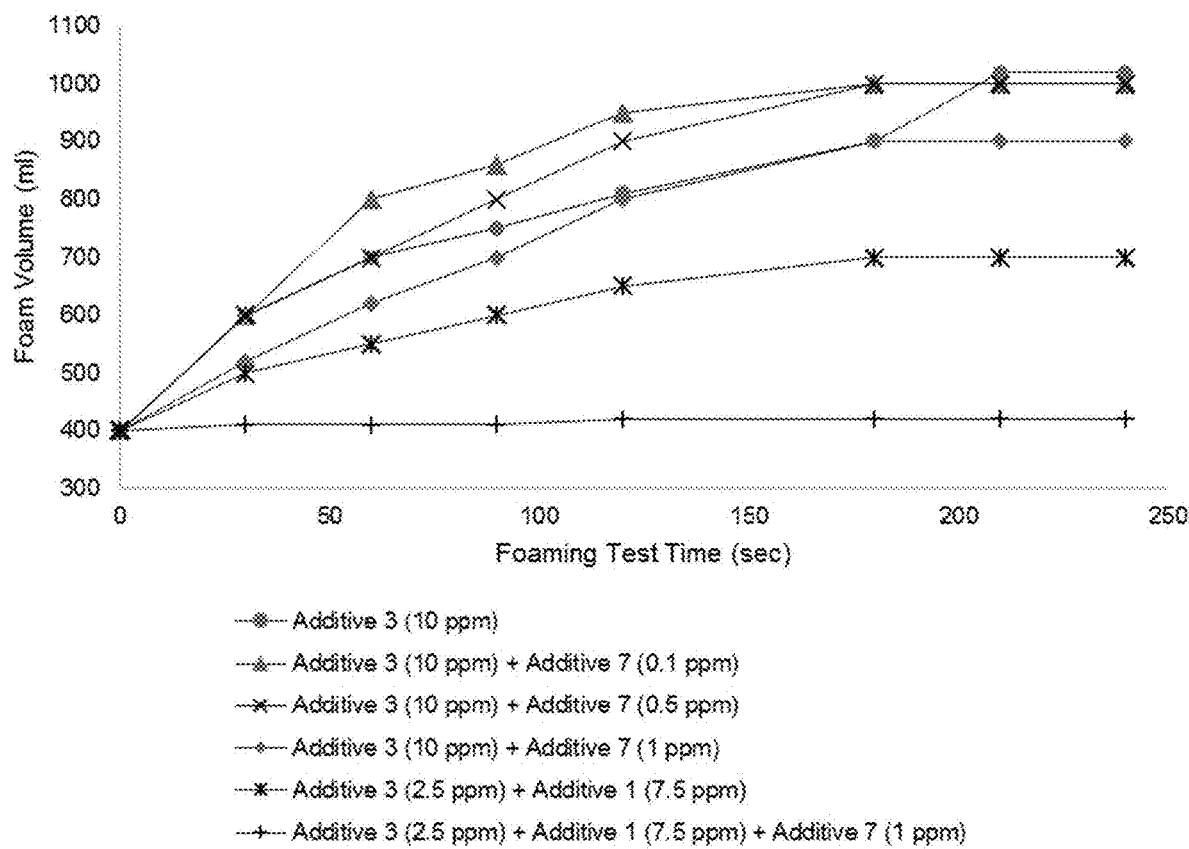
FIG. 2 shows foam volume over time when treated with different combinations of additives.

Foaming height and foam density were tested using different combinations of additives. An anti-foaming agent, Additive 7, was tested in combination with Additive 3 and Additive 1. About 400 ml of solution was added to a graduated cylinder and the solution was purged with nitrogen at a constant flow for about 3 minutes. Nitrogen purging generates foam at the liquid surface and the foam height can be determined from the markings on the graduated cylinder. The height of the foam was recorded at certain time intervals. FIG. 2 and Table 5 show that the combination of Additive 1, Additive 3, and Additive 7 resulted in significantly less foam volume.

TABLE 5

Foaming test results

| Time (sec) | Additive 3 (10 ppm) | Additive 3 (10 ppm) + Additive 7 (0.1 ppm) | Additive 3 (10 ppm) + Additive 7 (0.5 ppm) | Additive 3 (10 ppm) + Additive 7 (1 ppm) | Additive 3 (2.5 ppm) + Additive 1 (7.5 ppm) | Additive 3 (2.5 ppm) + Additive 1 (7.5 ppm) + Additive 7 (1 ppm) |
|---|---|---|---|---|---|---|
| 0 | 400 | 400 | 400 | 400 | 400 | 400 |
| 30 | 600 | 600 | 600 | 520 | 500 | 410 |
| 60 | 700 | 800 | 700 | 620 | 550 | 410 |
| 90 | 750 | 860 | 800 | 700 | 600 | 410 |
| 120 | 810 | 950 | 900 | 800 | 650 | 420 |
| 180 | 900 | 1000 | 1000 | 900 | 700 | 420 |
| 210 | 1020 | 1000 | 1000 | 900 | 700 | 420 |
| 240 | 1020 | 1000 | 1000 | 900 | 700 | 420 |

Example 4

The cleaning rate of Additive 3 was compared to the cleaning rate of a commercial product, BCP2175. BCP2175 comprises alkylamide hydrolysates, propylene glycol (CAS 57-55-6), and water. A nozzle having sulfur deposits was weighed and then immersed into a water tank that was maintained at a constant temperature and pH. About 40 liters of water was added to a tank, and the water was circulated through a monitoring unit that recorded pH, temperature, and turbidity. The temperature of the water was maintained at about 40° C. The pH was maintained at about 8. Additive 3 or BCP2175 was added at a given concentration. Water samples were collected periodically and analyzed for elemental sulfur, sulfate, sulfide, turbidity, and pH. After about 3 days of soaking the nozzle in the treated water, the nozzle was removed, dried in an oven, and weighed. The difference between the initial weight and final weight the amount of deposit removed from the nozzle.

TABLE 6

Nozzle cleaning results

| Additive | Initial Nozzle Weight (grams) | Final Nozzle Weight (grams) | Weight Loss (grams) | Amount Added (grams) | Observations |
|---|---|---|---|---|---|
| BCP2175 | 228.7 | 227.0 | 1.7 | 40 (6 active) | A thin deposit formed on the inside of the tank and the water heater. |
| Additive 3 | 245.8 | 243.65 | 2.15 | 8 (4 active) | No deposit layer in the tank and little to no deposit on the water heater. |

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated. In addition, unless expressly stated to the contrary, use of the term "a" is intended to include "at least one" or "one or more." For example, "a dispersant" is intended to include "at least one dispersant" or "one or more dispersants."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of dispersing sulfur, comprising:
   adding a first sulfur dispersant to process water containing elemental sulfur, wherein the first sulfur dispersant comprises a $C_5$-$C_{25}$ alkyl polyglycoside; and
   dispersing the elemental sulfur.

2. The method of claim 1, further comprising adding a second sulfur dispersant to the process water.

3. The method of claim 2, wherein the second sulfur dispersant comprises a polymer comprising acrylic acid and 2-acrylamido-2-methylpropane sulfonic acid.

4. The method of claim 2, further comprising blending the first sulfur dispersant and the second sulfur dispersant to form a dispersant mixture before addition to the process water.

5. The method of claim 4, wherein the dispersant mixture comprises from about 5% to about 95% by weight of the first sulfur dispersant and from about 95% to about 5% by weight of the second sulfur dispersant.

6. The method of claim 1, further comprising adding an anti-foaming agent to the process water.

7. The method of claim 6, wherein the anti-foaming agent is selected from a $C_5$-$C_{25}$ alkyl alcohol, a $C_5$-$C_{25}$ alkyl alcohol ethoxylate, monobasic aluminum stearate, stearic acid, polydimethylsiloxane, sorbitan monostearate, hydrated silica, ethoxylated sorbitan monostearate, xanthan gum, amorphous silica, and any combination thereof.

8. The method of claim 6, wherein the anti-foaming agent comprises polydimethylsiloxane and sorbitan monostearate.

9. The method of claim 1, wherein the first sulfur dispersant comprises a $C_{10-16}$ alkyl polyglycoside.

10. The method of claim 1, wherein the first sulfur dispersant comprises a $C_{10-16}$ alkyl polyglycoside and a $C_{8-10}$ alkyl polyglycoside.

11. The method of claim 3, wherein the polymer comprises about 50-70 wt % acrylic acid and about 30-50 wt % 2-acrylamido-2-methylpropane sulfonic acid.

12. The method of claim 3, wherein the polymer comprises a weight average molecular weight of about 5,000 Da to about 50,000 Da.

13. The method of claim 1, wherein the first sulfur dispersant is added to the process water in an amount of about 1 ppm to about 1000 ppm.

14. The method of claim 2, wherein the second sulfur dispersant is added to the process water in an amount of about 2 ppm to about 100 ppm.

15. The method of claim 1, wherein the first sulfur dispersant is added to the process water in an amount of about 1 ppm to about 10 ppm.

16. The method of claim 1, wherein the process water is geothermal cooling water or geothermal condensate.

17. A method of dispersing sulfur in geothermal cooling water, comprising:
   adding a first sulfur dispersant comprising $C_5$-$C_{25}$ alkyl polyglycoside to the geothermal cooling water containing elemental sulfur;
   adding a second sulfur dispersant comprising a polymer comprising acrylic acid and 2-acrylamido-2-methylpropane sulfonic acid to the geothermal cooling water; and
   dispersing the elemental sulfur.

18. The method of claim 17, wherein the first sulfur dispersant is added before the second sulfur dispersant, after the second sulfur dispersant, and/or as a mixture with the second sulfur dispersant.

* * * * *